(12) United States Patent
Federoff et al.

(10) Patent No.: US 10,578,629 B2
(45) Date of Patent: Mar. 3, 2020

(54) BIOMARKERS FOR MEMORY LOSS

(71) Applicants: Georgetown University, Washington, DC (US); University of Rochester, Rochester, NY (US)

(72) Inventors: Howard J. Federoff, Washington, DC (US); Mark E. Mapstone, Rochester, NY (US); Amrita K. Cheema, Washington, DC (US); Massimo S. Fiandaca, Washington, DC (US)

(73) Assignees: GEORGETOWN UNIVERSITY, Washington, DC (US); UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/134,976

(22) Filed: Apr. 21, 2016

(65) Prior Publication Data

US 2016/0238622 A1 Aug. 18, 2016

Related U.S. Application Data

(63) Continuation of application No. PCT/US2014/061578, filed on Oct. 21, 2014.

(60) Provisional application No. 61/893,762, filed on Oct. 21, 2013.

(51) Int. Cl.
*G01N 33/92* (2006.01)

(52) U.S. Cl.
CPC ......... *G01N 33/92* (2013.01); *G01N 2405/00* (2013.01); *G01N 2405/04* (2013.01); *G01N 2570/00* (2013.01); *G01N 2800/2821* (2013.01); *G01N 2800/52* (2013.01)

(58) Field of Classification Search
CPC . A61P 25/28; A61P 25/00; G01N 2800/2821; G01N 33/6896; G01N 2800/2814; G01N 2800/56; G01N 2500/20; G01N 2800/28; G01N 2800/50; G01N 33/92; G01N 2800/52; G01N 2405/04; G01N 2405/08; A61K 2300/00; C12P 7/6436; C12P 7/64
See application file for complete search history.

(56) References Cited

U.S. PATENT DOCUMENTS

2009/0029473 A1 1/2009 Han
2009/0305323 A1 12/2009 Kaddurah-Daouk et al.

FOREIGN PATENT DOCUMENTS

WO 2012/168561 A1 12/2012

OTHER PUBLICATIONS

Han et al., PLoS ONE, 6(7):e21643, Jul. 2011.*
Jones et al., Progress in Lipid Research, 49: 61-75, published online Aug. 2009.*
Rubio et al., J Neurolog Sci., 155:192-195, 1998.*
Astarita et al., "Towards a whole-body systems [multi-organ] lipidomics in Alzheimer's disease," Prostaglandins Leukot Essent Fatty Acids, 85(5):197-203 (2011).
Chan et al., "Comparative lipidomic analysis of mouse and human brain with Alzheimer disease," J. Biol. Chem., 287(4):2678-2688 (2012).
Han et al., "Multi-dimensional mass spectrometry-based shotgun lipidomics and the altered lipids at the mild cognitive impairment stage of Alzheimer's disease," Biochim Biophys Acta., 1801(8):774-783 (2010).
International Search Report and Written Opinion issued in a corresponding International Application No. PCT/US2014/061578 dated Feb. 5, 2015.

* cited by examiner

*Primary Examiner* — Kimberly Ballard
*Assistant Examiner* — Stacey N MacFarlane
(74) *Attorney, Agent, or Firm* — Haug Partners LLP (57) ABSTRACT

The present invention relates to methods of determining if a subject has an increased risk of suffering from memory impairment. The methods comprise analyzing at least one plasma sample from the subject to determine a value of the subject's lipidomic profile, and comparing the value of the subject's lipidomic profile with the value of a normal lipidomic profile. A decrease in the value of the subject's lipidomic profile over normal values is indicative that the subject has an increased risk of suffering from memory impairment compared to a normal individual.

18 Claims, 4 Drawing Sheets

BIOMARKERS FOR MEMORY LOSS

STATEMENT REGARDING FEDERALLY SPONSORED RESEARCH OR DEVELOPMENT

Part of the work performed during development of this invention utilized U.S. Government funds under National Instituted of Health Grant No. R01 AG030753 and Department of Defense Contract No. W81XWH-09-1-0107. The U.S. Government has certain rights in this invention.

BACKGROUND OF THE INVENTION

Field of the Invention

The present invention relates to methods of determining if a subject has an increased risk of suffering from memory impairment. The methods comprise analyzing at least one plasma sample from the subject to determine a value of the subject's lipidomic profile, and comparing the value of the subject's lipidomic profile with the value of a normal lipidomic profile. A decrease in the value of the subject's lipidomic profile over normal values is indicative that the subject has an increased risk of suffering from memory impairment compared to a normal individual.

Background of the Invention

Alzheimer's disease (AD) is a neurodegenerative disorder characterized by a progressive dementia that insidiously and inexorably robs older adults of their memory and other cognitive abilities. The prevalence of AD is expected to double every 20 years from 35.6 million individuals worldwide in 2010 to 115 million affected individuals by 2050. There is no cure and current therapies are unable to slow the disease progression.

Early detection of the at-risk population (preclinical), or those in the initial symptomatic stages (prodromal) of AD, may present opportunities for more successful therapeutic intervention, or even disease prevention by interdicting the neuropathological cascade that is characterized by the deposition of extracellular β-amyloid (Aβ) and accumulation of intracellular fibrils of microtubular hyperphosphorylated tau protein within the brain. Biomarkers for early disease, including cerebrospinal fluid (CSF) tau and Aβ levels, structural and functional magnetic resonance imaging (MRI), and the recent use of brain amyloid imaging, are of limited use for widespread screening since they provide diagnostic options that are either invasive, i.e., require lumbar puncture, time-consuming, i.e., several hours in a scanner for most comprehensive imaging protocols, or expensive. No current blood-based biomarkers can detect incipient dementia with the required sensitivity and specificity at a preclinical stage. Continued interest in blood-based biomarkers remains because these specimens are obtained using rapid, minimally invasive methods. With recent technological advances in 'omics' and systems level approaches, the comprehensive bioinformatic analyses of prognostic biomarkers may yield new insights into the underlying mechanisms and pathobiological networks of AD and possibly herald the development of new therapeutic strategies.

The preclinical interval resulting in mild cognitive impairment (MCI) or AD is known to be variable, multifactorial, and extends up to 7-10 years prior to the emergence of clinical signs. In the absence of valid and reliable biomarkers, multimodal neurocognitive testing remains the most accurate, standardized, and widely used pre-mortem screening method to determine clinical MCI or AD. The utility of strict cognitive assessment for preclinical states of MCI or AD is limited, however, as this approach is time-consuming and expected to be present almost all individuals as normal, as it quantitatively delineates specific brain properties, such as language, thought, and behavior, which is typically not affected in individual in the preclinical state. Thus, information obtained from multiple diagnostic studies will probably be most useful in defining the MCI/AD preclinical state, including neuropsychological testing and some form(s) of biomarker(s). While CSF and neuroimaging have been used to define preclinical MCI/AD to date, their clinical utility as screening tools for asymptomatic individuals is not established.

SUMMARY OF THE INVENTION

The present invention relates to methods of determining if a subject has an increased risk of suffering from memory impairment. The methods comprise analyzing at least one plasma sample from the subject to determine a value of the subject's lipidomic profile, and comparing the value of the subject's lipidomic profile with the value of a normal lipidomic profile. A decrease in the value of the subject's lipidomic profile over normal values is indicative that the subject has an increased risk of suffering from memory impairment compared to a normal individual.

BRIEF DESCRIPTION OF THE DRAWINGS

FIG. 1 depicts box and whisker plots of the combined discovery and validation samples on the five composite Z-score measures. The performance of the Converter group after phenoconversion ($C_{post}$) is plotted for direct comparison. The line centered on 0 in each plot represents the median Z-score on that measure for the entire cohort. The horizontal line in each plot represents the cut-off for impairment (−1.35 SD). Error bars represent s.e.m. Note that while significant decline is seen in the converters on $Z_{exe}$, $Z_{lan}$, and $Z_{mem}$, this is most noticeable in $Z_{mem}$ where all converters had non-impaired memory a baseline and impaired memory after conversion. NC=Normal Control (n=73); $C_{pre}$=Converters at baseline (n=28); $C_{post}$=Converters after conversion (n=28); MCI/AD=amnesiatic mild cognitive impairment or AD (n=46).

FIG. 2 depicts a trend plot for select metabolites showing differential abundance in each study group. SID-MRM-MS (stable isotope dilution-multiple reaction monitoring mass spectrometry) based quantitative profiling data were subjected to the non-parametric Kruskal Wallis test using the STAT pack module (Biocrates Inc.). The results are shown for a panel of metabolites in the normal controls (NC) (n=53), Converter$_{pre}$ (Con$_{pre}$) (n=18), Converter$_{post}$ (n=18) and MCI/AD (n=35) and groups. The abundance is plotted as absolute concentrations units (nM) extrapolated form the standard curve and normalized to the abundance of the stable isotope for the respective metabolite for the different study groups. The solid line represents the median abundance for the given group, while the dotted line represents mean abundance (error bars are s.d.). QC shows the scatter in the quality control samples. Figure Legend—A: Normal, B: Converter$_{pre}$, C: Converter$_{post}$, D: aMCI/AD, E: Super Normal, QC: Quality Control.

FIG. 4 depicts receiver operating characteristic (ROC) results for the lipidomics analyses. These plots show the ROC results from the models derived from the three phases of the lipidomics analysis. Simple logistic models based on the metabolites identified in each phase of the lipidomics analysis were developed and applied to determine the success of the models for classifying the Converter$_{pre}$ and Normal Control (NC) groups. The graphed lines represent the AUC obtained from the LASSO analysis (a), the targeted analysis of the ten metabolites in the discovery phase (b), and the application of the ten metabolite panel developed from the targeted discovery phase in the independent validation phase (c). The ROC plots represent sensitivity (i.e., true positive rate) vs. 1-specificity (i.e., false positive rate).

DETAILED DESCRIPTION OF THE INVENTION

The present invention relates to methods of determining if a subject has an increased risk of suffering from memory impairment. The methods comprise analyzing at least one plasma sample from the subject to determine a value of the subject's lipidomic profile, and comparing the value of the subject's lipidomic profile with the value of a normal lipidomic profile. A decrease in the value of the subject's lipidomic profile over normal values is indicative that the subject has an increased risk of suffering from memory impairment compared to a normal individual.

As used herein, the term subject or "test subject" indicates a mammal, in particular a human or non-human primate. The test subject may or may not be in need of an assessment of a predisposition to memory impairment. For example, the test subject may have a condition or may have been exposed to injuries or conditions that are associated with memory impairment prior to applying the methods of the present invention. In another embodiment, the test subject has not been identified as a subject that may have a condition or may have been exposed to injuries or conditions that are associated with memory impairment prior to applying the methods of the present invention.

As used herein, the phrase "memory impairment" means a measurable or perceivable decline or decrease in the subject's ability to recall past events. As used herein, the term "past events" includes both recent (new) events (short-term memory) or events further back in time (long-term memory). In one embodiment, the methods are used to assess an increased risk short-term memory impairment. In another embodiment, the methods are used to assess an increased risk in long-term memory impairment. The measurable or perceivable decline in the subject's ability to recall past events may be assessed clinically by a health care provider, such as a physician, physician's assistant, nurse, nurse practitioner, psychologist, psychiatrist, hospice provider, or any other provider that can assess a subject's memory. The measurable or perceivable decline in the subject's ability to recall past events may be assessed in a less formal, non-clinical manner, including but not limited to the subject himself or herself, acquaintances of the subject, employers of the subject and the like. The invention is not limited to a specific manner in which the subject's ability to recall past events is assessed. In fact, the methods of the invention can be implemented without the need to assess a subject's ability to recall past events. Of course, the methods of the present invention may also include assessing the subject's ability to assess past events one or more times, both before determining the subject's lipidomic profile and after determining the subject's lipidomic profile at least one time.

In one embodiment, the decline or decrease in the ability to recall past events is relative to each individual's ability to recall past events prior to the diagnosed decrease or decline in the ability to recall past events. In another embodiment, the decline or decrease in the ability to recall past events is relative to a population's (general, specific or stratified) ability to recall past events prior to the diagnosed decrease or decline in the ability to recall past events.

As used herein, the term means "increased risk" is used to mean that the test subject has an increased chance of developing or acquiring memory impairment compared to a normal individual. The increased risk may be relative or absolute and may be expressed qualitatively or quantitatively. For example, an increased risk may be expressed as simply determining the subject's lipidomic profile and placing the patient in an "increased risk" category, based upon previous population studies. Alternatively, a numerical expression of the subject's increased risk may be determined based upon the lipidomic profile. As used herein, examples of expressions of an increased risk include but are not limited to, odds, probability, odds ratio, p-values, attributable risk, relative frequency, positive predictive value, negative predictive value, and relative risk.

For example, the correlation between a subject's lipidomic profile and the likelihood of suffering from memory impairment may be measured by an odds ratio (OR) and by the relative risk (RR). If $P(R^+)$ is the probability of developing memory impairment for individuals with the risk profile (R) and $P(R^-)$ is the probability of developing memory impairment for individuals without the risk profile, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a lipidomic risk profile in cases studies and $F^-$ is the frequency of lipidomic risk profile in controls. $F^+$ and $F^-$ can be calculated using the lipidomic risk profile frequencies of the study.

The attributable risk (AR) can also be used to express an increased risk. The AR describes the proportion of individuals in a population exhibiting memory impairment due to a specific member of a lipidomic risk profile. AR may also be important in quantifying the role of individual components (specific member) in disease etiology and in terms of the public health impact of the individual marker. The public health relevance of the AR measurement lies in estimating the proportion of cases of memory impairment in the population that could be prevented if the profile or individual component were absent. AR may be determined as follows: $AR=P_E(RR-1)/(P_E(RR-1)+1)$, where AR is the risk attributable to a profile or individual component of the profile, and $P_E$ is the frequency of exposure to a profile or individual component of the profile within the population at large. RR is the relative risk, which can be approximated with the odds ratio when the profile or individual component of the profile under study has a relatively low incidence in the general population.

In one embodiment, the increased risk of a patient can be determined from p-values that are derived from association studies. Specifically, associations with specific profiles can be performed using regression analysis by regressing the lipidomic profile with memory impairment. In addition, the regression may or may not be corrected or adjusted for one or more factors. The factors for which the analyses may be adjusted include, but are not limited to age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's apolipoprotein epsilon (ApoE) genotype to name a few.

Increased risk can also be determined from p-values that are derived using logistic regression. Binomial (or binary) logistic regression is a form of regression which is used when the dependent is a dichotomy and the independents are of any type. Logistic regression can be used to predict a dependent variable on the basis of continuous and/or categorical independents and to determine the percent of variance in the dependent variable explained by the independents; to rank the relative importance of independents; to assess interaction effects; and to understand the impact of covariate control variables. Logistic regression applies maximum likelihood estimation after transforming the dependent into a "log it" variable (the natural log of the odds of the dependent occurring or not). In this way, logistic regression estimates the probability of a certain event occurring. These analyses are conducted with the program SAS.

SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and non-parametric analysis.

As used herein, the phrase "lipidomic profile" means a collection of measurements, such as but not limited to a quantity or concentration, for individual molecules taken from a test sample of the subject. Examples of test samples or sources of components for the lipidomic profile include, but are not limited to, biological fluids, which can be tested by the methods of the present invention described herein, and include but are not limited to whole blood, serum, plasma, cerebrospinal fluid, urine, amniotic fluid, lymph fluids, and various external secretions of the respiratory, intestinal and genitourinary tracts, tears, saliva, milk, white blood cells, myelomas and the like. Test samples to be assayed also include but are not limited to tissue specimens including normal and abnormal tissue.

Techniques to assay levels of individual components of the lipidomic profile from test samples are well known to the skilled technician, and the invention is not limited by the means by which the components are assessed. In one embodiment, levels of the individual components of the lipidomic profile are assessed using mass spectroscopy, high-performance liquid chromatography (HPLC) and the like. Other methods of assessing levels of the individual components include biological methods, such as but not limited to ELISA assays.

The assessment of the levels of the individual components of the lipidomic profile can be expressed as absolute or relative values and may or may not be expressed in relation to another component, a standard an internal standard or another molecule of compound known to be in the sample. If the levels are assessed as relative to a standard or internal standard, the standard may be added to the test sample prior to, during or after sample processing.

To assess levels of the individual components of the lipidomic profile, a sample is taken from the subject. The sample may or may not processed prior assaying levels of the components of the lipidomic profile. For example, whole blood may be taken from an individual and the blood sample may be processed, e.g., centrifuged, to isolate plasma or serum from the blood. The sample may or may not be stored, e.g., frozen, prior to processing or analysis.

Individual components of the lipidomic profile include but are not limited to phosphatidyl cholines (PC) lyso PCs and acylcarnitines (AC). Specific examples of PCs, lyso PCs and ACs that can be included as constituents of the lipidomic profile include but are not limited to (1) propionyl AC, (2) lyso PC a C18:2, (3) PC aa C36:6, (4) C16:1-OH (Hydroxyhexadecenoyl-L-carnitine), (5) PC aa C38:0, (6) PC aa C38:6, (7) PC aa C40:1, (8) PC aa C40:2, (9) PC aa C40:6 and (10) PC ae C40:6. Those of skill in the art will recognize the specific identity of each constituent listed based upon the nomenclature above. For example, metabolite (5) (PC aa C38:0) is known to those of skill in the art as phosphatidylcholine diacyl C 38:0, metabolite (10) (PC ae C40:6) is known as phosphatidylcholine acyl-alkyl C 40:6 and metabolite (2) (lyso PC a C18:2) is known as lysoPhosphatidylcholine acyl C18:2.

For the purposes of the present invention the lipidomic profile comprises at least two, three, four, five, six, seven, eight, nine or all ten metabolites listed above. If two metabolites are used in generating the lipidomic profile, any combination of two of 1-10 listed above can be used. If three metabolites are used in generating the lipidomic profile, any combination of three of 1-10 listed above can be used. If four metabolites are used in generating the lipidomic profile, any combination of four of 1-10 listed above can be used. If five metabolites are used in generating the lipidomic profile, any combination of five of 1-10 listed above can be used. If six metabolites are used in generating the lipidomic profile, any combination of six of 1-10 listed above can be used. If seven metabolites are used in generating the lipidomic profile, any combination of seven of 1-10 listed above can be used. If eight metabolites are used in generating the lipidomic profile, any combination of eight of 1-10 listed above can be used. If nine metabolites are used in generating the lipidomic profile, any combination of nine of 1-10 listed above can be used. Of course, all ten metabolites of 1-10 above can be used to generate the lipidomic profile.

The subject's lipidomic profile is compared to the profile that is deemed to be a normal lipidomic profile. To establish the lipidomic profile of a normal individual, an individual or group of individuals may be first assessed for their ability to recall past events to establish that the individual or group of individuals has a normal or acceptable ability memory. Once established, the lipidomic profile of the individual or group of individuals can then be determined to establish a "normal lipidomic profile." In one embodiment, a normal lipidomic profile can be ascertained from the same subject when the subject is deemed to possess normal cognitive abilities and no signs (clinical or otherwise) of memory impairment. In one embodiment, a "normal" lipidomic profile is assessed in the same subject from whom the sample is taken prior to the onset of measurable, perceivable or diagnosed memory impairment. That is, the term "normal" with respect to a lipidomic profile can be used to mean the subject's baseline lipidomic profile prior to the onset of memory impairment. The lipidomic profile can then be reassessed periodically and compared to the subject's baseline lipidomic profile. Thus, the present invention also include methods of monitoring the progression of memory impairment in a subject, with the methods comprising determining the subject's lipidomic profile more than once over a period of time. For example, some embodiments of the methods of the present invention will comprise determining the subject's lipidomic profile two, three, four, five, six, seven, eight, nine, 10 or even more times over a period of time, such as a year, two years, three, years, four years, five years, six years, seven years, eight years, nine years or even 10 years or longer. The methods of monitoring a subject's risk of having memory impairment would also include embodiments in which the subject's lipidomic profile is assessed during and after treatment of memory impairment. In other words, the present invention also includes methods of monitoring the efficacy of treatment of memory impairment by assessing the subject's lipidomic profile over the course of the treatment and after the treatment. The treatment may be any treatment designed to increase a subject's ability to recall past events, i.e., improve a subject's memory.

In another embodiment, a normal lipidomic profile is assessed in a sample from a different subject or patient (from the subject being analyzed) and this different subject does not have or is not suspected of having memory impairment. In still another embodiment, the normal lipidomic profile is assessed in a population of healthy individuals, the constituents of which display no memory impairment. Thus, the subject's lipidomic profile can be compared to a normal lipidomic profile generated from a single normal sample or a lipidomic profile generated from more than one normal sample.

Of course, measurements of the individual components, e.g., concentration, of the normal lipidomic profile can fall within a range of values, and values that do not fall within this "normal range" are said to be outside the normal range. These measurements may or may not be converted to a value, number, factor or score as compared to measurements in the "normal range." For example, a measurement for a specific metabolite that is below the normal range, may be assigned a value or −1, −2, −3, etc., depending on the scoring system devised.

In one embodiment, the "lipidomic profile value" can be a single value, number, factor or score given as an overall collective value to the individual components of the profile. For example, if each component is assigned a value, such as above, the lipidomic value may simply be the overall score of each individual value. For example, if 10 components are used to generate the lipidomic profile and five of the components are assigned values of "−2" and five are assigned values of "−1," the lipidomic value in this example would be −15, with a normal value being "0." In this manner, the lipidomic profile value could be useful single number or score, the actual value or magnitude of which could be an indication of the actual risk of memory impairment, e.g., the "more negative" the value, the greater the risk of memory impairment.

In another embodiment the "lipidomic profile value" can be a series of values, numbers, factors or scores given to the individual components of the profile. In another embodiment, the "lipidomic profile value" may be a combination of values, numbers, factors or scores given to individual components of the profile as well as values, numbers, factors or scores collectively given to a group of components. For example, the measurements of the phosphatidyl cholines in the profile may be grouped into one composite score and individual acylcarnitines may be grouped into another composite score. In another example, the lipidomic profile value may comprise or consist of individual values, number, factors or scores for specific components, e.g., metabolite 3 (PC aa C36:6), as well as values, numbers, factors or scores for a group on components.

Figure 2:
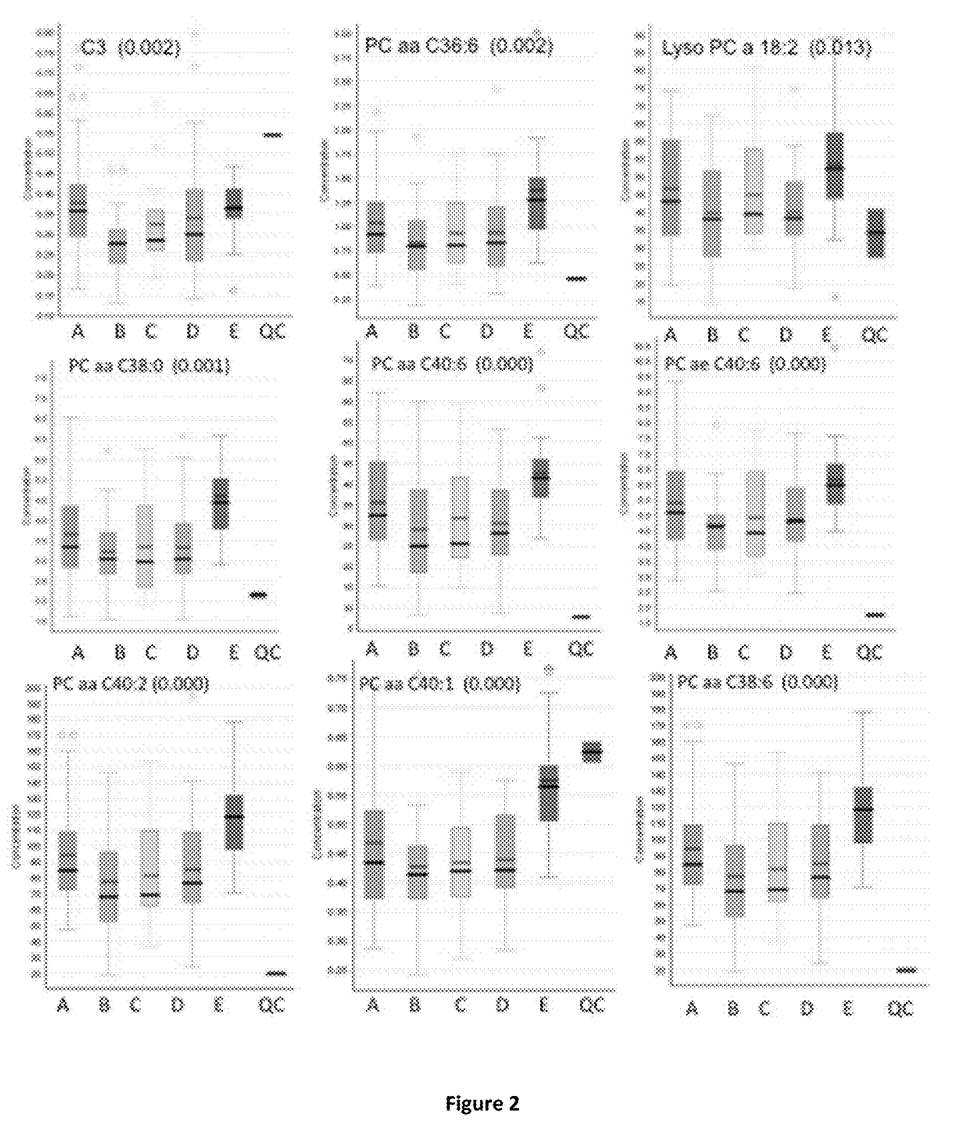

In another embodiment, the value of the lipidomic profile can be the collection of data from the individual measurements and need not be converted to a scoring system, such that the "lipidomic profile value" is a collective of the individual measurements of the individual components of the profile. For example, the value of the lipidomic profile may be a collective of measurements as seen in FIG. 2.

If it is determined that a subject has an increased risk of memory impairment, the attending health care provider may subsequently prescribe or institute a treatment program. In this manner, the present invention also provides for methods of screening individuals as candidates for treatment of memory impairment. The attending healthcare worker may begin treatment, based on the subject's lipidomic profile, before there are perceivable, noticeable or measurable signs of memory impairment in the individual.

Similarly, the invention provides methods of monitoring the effectiveness of a treatment for memory impairment. Once a treatment regimen has been established, with or without the use of the methods of the present invention to assist in a diagnosis of memory impairment, the methods of monitoring a subject's lipidomic profile over time can be used to assess the effectiveness of a memory impairment treatment. Specifically, the subject's lipidomic profile can be assessed over time, including before, during and after treatments for memory impairment. The lipidomic profile can be monitored, with a decline in the values of the profile over time being indicative that the treatment may not be as effective as desired.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety

EXAMPLES

Example 1

Neurocognitive Methods

A total of 525 volunteers participated in this study as part of the Rochester/Orange County Aging Study (R/OCAS), an ongoing natural history study of cognition in community-dwelling older adults. Briefly, participants were followed with yearly cognitive assessments and blood samples were collected following an overnight fast and withholding of all medications. At baseline and each yearly visit, participants completed assessments in such as activities in daily living, memory complaints, signs and symptoms of depression, and were administered a detailed cognitive assessment.

For this study, data from the cognitive tests were used to classify participants into groups for biomarker discovery. Standardized scores (Z-scores) were derived for each participant on each cognitive test and the composite Z-scores were computed for five cognitive domains (attention, executive, language, memory, visuoperceptual) (Table).

TABLE 1

| Attention ($Z_{att}$) | Executive ($Z_{exe}$) | Language ($Z_{lan}$) | Visuoperceptual ($Z_{vis}$) | Memory ($Z_{mem}$) |
|---|---|---|---|---|
| Wechsler Memory Scale-III Forward Digit Span (WMS-III FDS) | Wechsler Memory Scale-III Backward Digit Span (WMS-III BDS) | 1-min Category fluency (Animals) | Hooper Visual Organization Test (HVOT) | Rey Auditory Verbal Learning Test Learning (RAVLT Learning) |
| Trail Making Test-Part A (TMT-A) | Trail Making Test-Part B (TMT-B) | Boston Naming Test 60-Item version (BNT-60) | | Rey Auditory Verbal Learning Test Retrieval (RAVLT Retrieval) Rey Auditory Verbal Learning Test Retention (RAVLT Recognition) |

Normative data for Z-score calculations were derived from the performance of the participants on each of the cognitive tests adjusted for age, education, sex, and visit. To reduce the effect of cognitively impaired participants on the mean and SD, age-, education-, sex, and visit-adjusted residuals from each domain Z-score model were robustly standardized to have median 0 and robust SD=1, where the robust SD=IQR/1.35, as 1.35 is the IQR (Inter-Quartile Range) of a standard normal distribution.

The participants were then categorized into groups of incident aMCI or early AD (combined into one category aMCI/AD), cognitively normal control (NC), and those who converted to MCI or AD over the course of the study (Converters) based on these composite scores. Impairment was defined as a Z-score 1.35 SD below the cohort median. All participants classified as aMCI met recently revised criteria for the amnestic subtype of MCI. Other behavioral phenotypes of MCI were excluded to concentrate on the amnestic form, which most likely represents nascent Alzheimer's pathology. All early AD participants met recently revised criteria for probable Alzheimer's disease with impairment in memory and at least one other cognitive domain. For the MCI and early AD groups, scores on the measures of memory complaints (MMQ) and activities of daily living (PGC-IADL) were used to corroborate research definitions of these states. All Converters had non-impaired memory at entry to the study ($Z_{mem} \geq -1.35$), developed memory impairment over the course of the study ($Z_{mem} \leq -1.35$) and met criteria for the above definitions of aMCI or AD. To enhance the specificity of the biomarker analyses, NC participants in this study were conservatively defined with $Z_{mem} \pm 1$ SD of the cohort median rather than simply $\geq -1.35$, and all other Z-scores $\geq -1.35$ SD.

For each subject, $Z_{mem}$(last), $Z_{att}$(last), $Z_{exe}$(last), $Z_{lan}$(last), and $Z_{vis}$(last) were defined as the age-gender-education-visit-adjusted robust Z-scores for the last available visit for each subject. The aMCI/AD group was defined as those participants whose adjusted $Z_{mem}$ was 1 IQR below the median at their last available visit, i.e., $Z_{mem}$(last)$\leq -1.35$. Converters were defined as that subset of the a MCI/AD group whose adjusted $Z_{mem}$ at baseline visit 0 was no more than 1 IQR below the median, i.e., $Z_{mem}$(visit=0)>-1.35 and $Z_{mem}$(last)$\leq -1.35$. Participants were classified as NC if they had central scores on all domains at both the first and last visits, i.e., only if they met all of the following six conditions: (i) $-1 < Z_{mem}$(last)$<1$, (ii) $-1 < Z_{mem}$(visit=0)$<1$, (iii) $Z_{min}$(last)>-1.35, (iv) $Z_{min}$(visit=0)>-1.35, (v) $Z_{max}$(last) $<1.35$, and (vi) $Z_{max}$(visit=0)$<1.35$, where $Z_{max}$(last) and $Z_{max}$(visit=0) denote the maximum of the five adjusted Z-scores at the last and first visits, respectively. $Z_{mem}$ for normal participants had to be within 0.74 IQR (1 SD) of the median, rather than just 1 IQR (1.35 SD), to guarantee that they were >0.25 IQR (0.35 SD) from aMCI/AD participants.

After three years of being in the study, (December, 2010), 202 participants had completed a baseline and two yearly visits. At the third visit, 53 participants met criteria for aMCI/AD and 96 met criteria for NC. Of the 53 aMCI/AD participants, 18 were Converters and 35 were incident aMCI or AD. The remaining 53 participants did not meet the criteria for either group and were not considered for biomarker profiling. Some of these individuals met criteria for non-amnestic MCI and many had borderline or even above average memory scores that precluded their inclusion as either a MCI/AD or NC. 53 of the NC participants were matched to the 53 aMCI/AD participants based on sex, age, and education level. Blood samples were obtained on the last available study visit for the 53 MCI/AD and the 53 NC for biomarker discovery. Two blood samples from each of the 18 Converters were also included: one from the baseline visit (Converter$_{pre}$) when $Z_{mem}$ was non-impaired and one from the third visit (Converter$_{post}$) when $Z_{mem}$ was impaired and they met criteria for either aMCI or AD. Thus, at total of 124 samples from 106 participants were analyzed.

Internal cross-validation was employed to validate findings from the discovery phase. Blood samples for validation were identified at the end of the fifth year of the study and all 106 participants included in the discovery phase were excluded from consideration for the validation phase. Cognitive composite Z-scores were re-calculated based on the entire sample available and the same procedure and criteria were used to identify samples for the validation phase. A total of 145 participants met criteria for a group: 21 aMCI/AD and 124 NC. Of the 21 aMCI/AD, 10 were Converters. 20 of the NC participants were matched to the aMCI/AD participants on the basis of age, sex, and education level as in the discovery phase. In total, 41 participants contributed samples to the validation phase and, as before, the 10 Converters also contributed a baseline sample (Converter$_{pre}$) for a total of 51 samples.

Neurocognitive Statistical Analyses

The neurocognitive analyses were designed to demonstrate the general equivalence of the discovery and validation samples on clinical and cognitive measures. Separate Multivariate Analysis of Variance (MANOVA's) tests were used to examine discovery/validation group performance on the composite Z-scores and on self-report measures of memory complaints, memory related functional impairment, depressive symptoms, and a global measure of cognitive function. In the first MANOVA, biomarker sample (discovery, validation) was the independent variable and MMQ, IADL, GDS, and MMSE were the dependent variables. In the second MANOVA, biomarker sample (discovery, validation) was the independent variable and the five cognitive domain Z-scores ($Z_{att}$, $Z_{exe}$, $Z_{lan}$, $Z_{mem}$, and $Z_{vis}$) were the dependent variables. Significance was set at alpha=0.05 and Tukey's HSD procedure was used for post-hoc comparisons. All statistical analyses were performed using SPSS (version 21).

Lipidomics Methods

LC/MS-grade acetonitrile (ACN), Isopropanol (IPA), water and methanol were purchased from Fisher Scientific (New Jersey, USA). High purity formic acid (99%) was purchased from Thermo-Scientific (Rockford, Ill.). Debrisoquine, 4-Nitrobenzoic acid (4-NBA), Pro-Asn, Glycoursodeoxycholic acid, Malic acid, were purchased from Sigma (St. Louis, Mo., USA). All lipid standards including 14:0 LPA, 17:0 Ceramide, 12:0 LPC, 18:0 Lyso PI and PC(22:6/0:0) were procured from Avanti Polar Lipids Inc. (USA).

Metabolite Extraction

Briefly, the plasma samples were thawed on ice and vortexed. For metabolite extraction, 25 µL of plasma sample was mixed with 175 µL of extraction buffer (25% acetonitrile in 40% methanol and 35% water) containing internal standards [10 µL of debrisoquine (1 mg/mL), 50 µL of 4, nitro-benzoic acid (1 mg/mL), 27.3 µl of Ceramide (1 mg/mL) and 2.5 µL of LPA (lysophosphatidic acid) (4 mg/mL) in 10 mL). The samples were incubated on ice for 10 minutes and centrifuged at 14,000 rpm at 4° C. for 20 minutes. The supernatant was transferred to a fresh tube and dried under vacuum. The dried samples were reconstituted in 200 µL of buffer containing 5% methanol, 1% acetonitrile and 94% water. The samples were centrifuged at 13,000 rpm for 20 minutes at 4° C. to remove fine particulates. The supernatant was transferred to a glass vial for UPLC-ESI-Q-TOF-MS analysis.

UPLC-ESI-QTOF-MS Based Data Acquisition for Untargeted Lipidomic Profiling

Each sample (2 µL) was injected onto a reverse-phase CSH C18 1.7 µM 2.1×100 mm column using an Acquity H-class UPLC system (Waters Corporation, USA). The gradient mobile phase comprised of water containing 0.1% formic acid solution (Solvent A), 100% acetonitrile (Solvent B) and 10% acetonitrile in isopropanol (IPA) containing 0.1% formic acid and 10 mM Ammonium formate (Solvent C). Each sample was resolved for 13 minutes at a flow rate of 0.5 mL/min for 8 min and then 0.4 mL/min from 8 to 13 min. The UPLC gradient consisted of 98% A and 2% B for 0.5 min then a ramp of curve 6 to 60% B and 40% A from 0.5 min to 4.0 min, followed by a ramp of curve 6 to 98% B and 2% A from 4.0 to 8.0 min, then ramped to 5% B and 95% C from 9.0 min to 10.0 min at a flow rate of 0.4 ml/min, and finally to 98% A and 2% B from 11.0 min to 13 minutes. The column eluent was introduced directly into the mass spectrometer by electrospray ionization. Mass spectrometry was performed on a Quadrupole-Time of Flight (Q-TOF) instrument (Xevo G2 QTOF, Waters Corporation, USA) operating in either negative (ESI$^-$) or positive (ESI$^+$) electrospray ionization mode with a capillary voltage of 3200 V in positive mode and 2800 V in negative mode, and a sampling cone voltage of 30 V in both modes. The desolvation gas flow was set to 750 L h$^{-1}$ and the temperature was set to 350° C. while the source temperature was set at 120° C. Accurate mass was maintained by introduction of a lock spray interface of leucine-enkephalin (556.2771 [M+H]$^+$ or 554.2615 [M−H]$^−$) at a concentration of 2 pg/µl in 50% aqueous acetonitrile and a rate of 2 µl/min. Data were acquired in centroid MS mode from 50 to 1200 m/z mass range for TOF-MS scanning as single injection per sample and the batch acquisition was repeated to check experimental reproducibility. For the metabolomics profiling experiments, pooled quality control (QC) samples (generated by taking an equal aliquot of all the samples included in the experiment) were run at the beginning of the sample queue for column conditioning and every ten injections thereafter to assess inconsistencies that are particularly evident in large batch acquisitions in terms of retention time drifts and variation in ion intensity over time. This approach has been recommended and used as a standard practice by leading metabolomics researchers. A test mix of standard metabolites was run at the beginning and at the end of the run to evaluate instrument performance with respect to sensitivity and mass accuracy. The overlay of the total ion chromatograms of the quality control samples depicted excellent retention time reproducibility. The sample queue was randomized to remove bias. The TICs for each of the three groups showed characteristic patterns.

Stable Isotope Dilution-Multiple Reaction Monitoring Mass Spectrometry (SID-MRM-MS)

Targeted metabolomic analysis of plasma sample was performed using the Biocrates Absolute-IDQ P180 (BIOCRATES, Life Science AG, Innsbruck, Austria). This validated targeted assay allows for simultaneous detection and quantification of metabolites in plasma samples (10 µL) in a high throughput manner. The methods have been described in detail. The plasma samples were processed as per the instructions by the manufacturer and analyzed on a triple quadrupole mass spectrometer (Xevo TQ-S, Waters Corporation, USA) operating in the MRM mode. The measurements were made in a 96 well format for a total of 148 samples, seven calibration standards and three quality control samples were integrated in the kit.

Briefly, the flow injection analysis (FIA) tandem mass spectrometry (MS/MS) method was used to quantify a panel of 144 lipids simultaneously by multiple reaction monitoring. Absolute quantification was achieved by extrapolating from a standard curve. The other metabolites were resolved on the UPLC and quantified using scheduled MRMs. The kit facilitated absolute quantitation of 21 amino acids, hexose, carnitine, 39 acylcarnitines, 15 sphingomyelins, 90 phosphatidylcholines and 19 biogenic amines. Data analysis was performed using the MetIQ software (Biocrates) while the statistical analyses were performed using the STAT pack module v3 (Biocrates). The abundance was calculated from area under the curve by normalizing to the respective isotope labeled internal standard. The concentration is expressed as nmol/L. Quality control samples were used to assess reproducibility of the assay. The mean of the coefficient of variation (CV) for the 180 metabolites was 0.08 and 95% of the metabolites had a CV of <0.15.

Lipidomics Statistical Analyses

The m/z features of metabolites were normalized with log transformation that stabilized the variance followed with a quantile normalization to make the empirical distribution of intensities the same across samples. The metabolites were selected among all those known to be identifiable using a ROC regularized learning technique, based on the least absolute shrinkage and selection operator (LASSO) penalty as implemented with the R package 'glmnet', which uses cyclical coordinate descent in a pathwise fashion. The regularization path over a grid of values was obtained for the tuning parameter lambda through 10-fold cross-validation. The optimal value of the tuning parameter lambda, which was obtained by the cross-validation procedure, was then used to fit the model. All the features with non-zero coefficients were retained for subsequent analysis. The classification performance of the selected metabolites was assessed using area under the ROC (receiver operating characteristic) curve (AUC). The ROC can be understood as a plot of the probability of classifying correctly the positive samples against the rate of incorrectly classifying true negative samples. Thus the AUC measure of an ROC plot is actually a measure of predictive accuracy. To maintain rigor of independent validation, the simple logistic model with the ten metabolite panel was used, although a more refined model can yield greater AUC.

Results

Over the course of the study, 74 participants met criteria for either aMCI or mild AD, 46 of these were incidental cases at entry and 28 phenoconverted (Converters) from a non-impaired memory status at entry (Converter$_{pre}$). The average time to phenoconversion was 2.1 years (range=1-5 years). 53 aMCI/AD participants were selected, including 18 Converters, and 53 age-, education-, and sex-matched cognitively normal control (NC) participants for untargeted lipidomics biomarker discovery. Internal cross validation was used to evaluate the accuracy of the discovered lipidomics profile in classifying a blinded sample of 51 subjects consisting of the remaining subset of 21 aMCI/AD participants, including 10 Converters, and an additional 20 matched NC.

The aMCI/AD, Converter, and NC groups were defined primarily using a composite measure of memory performance in addition to composite measures of other cognitive abilities and clinical measures of memory complaints and functional capacities. (See Tables 1 and 2).

TABLE 2

| Clinical/Cognitive Measures | Dependent Measure (Range) | Domain Assessed |
|---|---|---|
| Multiple Assessment Inventory IADL Scale (MAI-IADL) Lawton MP. (1988) Instrumental Activities of Daily Living (IADL) scale: Original observer-rated version. *Psychopharmacology Bulletin*, 24, 785-7. | Total Score (0-27) | Functional capacities |
| Multifactorial Memory Questionnaire (MMQ) Troyer AK and Rich JB. (2002). Psychometric properties of a new metamemory questionnaire for older adults. *Journal of Gerontology*, 57(1), 19-27. | Total Score (0-228) | Memory complaints |
| Mini Mental State Examination (MMSE) Folstein, MF, Folstein, SE, and McHugh, PR. (1975). "Mini-mental state". *Journal of Psychiatric Research*, 12, 189-98. | Total Score (0-30) | Global cognitive ability |
| Geriatric Depression Scale-Short Form (GDS-SF) Sheikh JI and Yesavage JA. (1986). Geriatric Depression Scale (GDS): Recent evidence and development of a shorter version. *Clinical Gerontologist*, 5, 165-173. | Total Score (0-15) | Mood |
| Wechsler Memory Scale-III Forward Digit Span (WMS-III FDS) Wechsler D. *Wechsler Memory Scale-III Manual*. San Antonio, TX: The Psychological Corporation, 1997. | Span Length (0-9) | Attention |
| Trail Making Test-Part A (TMT-A) Reitan RM. (1958). Validity of the Trail Making Test as an indicator of organic brain damage. *Perceptual and Motor Skills*, 8, 271-6. | Completion time (1-300 seconds) | Attention |
| Wechsler Memory Scale-III Backward Digit Span (WMS-III BDS) Wechsler D. *Wechsler Memory Scale-III Manual*. San Antonio, TX: The Psychological Corporation, 1997. | Span Length (0-8) | Executive ability |
| Trail Making Test-Part B (TMT-B) Reitan RM. (1958). Validity of the Trail Making Test as an indicator of organic brain damage. *Perceptual and Motor Skills*, 8, 271-6. | Completion Time (1-300 seconds) | Executive ability |
| Category fluency (Animals) Borkowski J, Benton A, Spreen 0. (1967). Word fluency and brain damage. *Neuropsychologia*, 5, 135-140 | Animals named in 1-minute | Language |
| Boston Naming Test 60-Item version (BNT-60) Kaplan E, Goodglass H, and Weintraub S. (1983). Boston Naming Test. Philadelphia: Lea & Feibiger. | Total Correct (0-60) | Language |
| Rey Auditory Verbal Learning Test Learning (RAVLT Learning) Rey A. (1964). L'examen clinique en psychologie. Paris: Presses Universitaires de France. | Total words recalled over Trials 1-5 (0-75) | Verbal learning |
| Rey Auditory Verbal Learning Test Recall (RAVLT Retrieval) Rey A. (1964). L'examen clinique en psychologie. Paris: Presses Universitaires de France. | Words recalled at 20-minute delay (0-15) | Verbal retrieval |
| Rey Auditory Verbal Learning Test Retention (RAVLT Recognition) Rey A. (1964). L'examen clinique en psychologie. Paris: Presses Universitaires de France. | True positives-false positives (0-15) | Verbal retention |
| Hooper Visual Organization Test (HVOT) Hooper HE. Hooper Visual Organization Test (VOT) Los Angeles: Western Psychological Services; 1983. | Total score (0-30) | Visuoperception |

Figure 1:
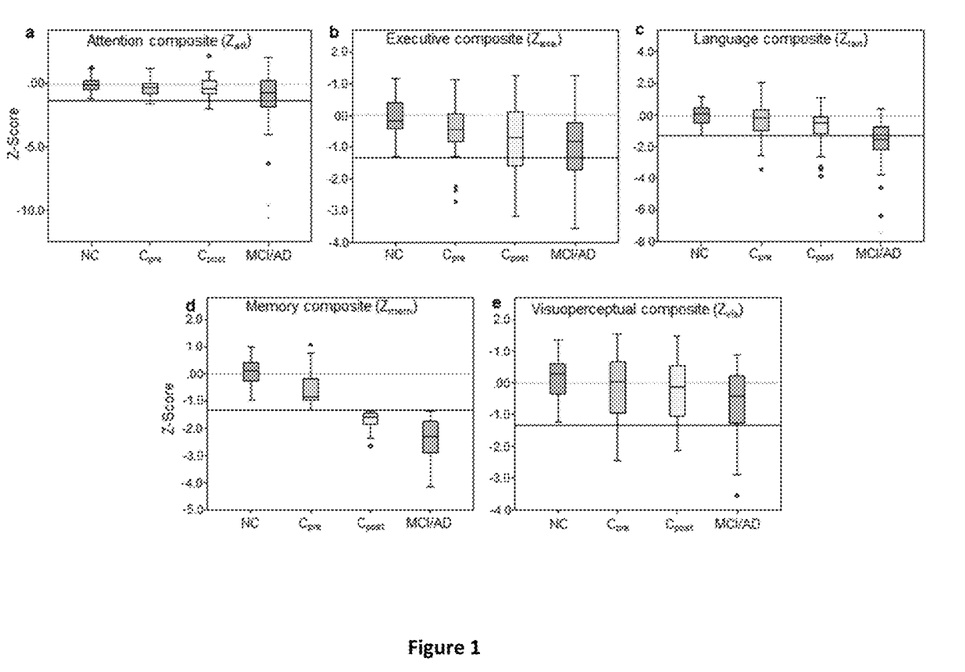

Plots of group means on the composite measures can be found in FIG. 1 and group means are reported in Table 3. The discovery and validation groups did not differ on clinical measures including self-reported memory complaints, functional impairment, depressive symptoms, and a global measure of cognition ($F(4,170)=1.376$, $p=0.244$), nor on any composite Z-score ($F(5,169)=2.118$, $p=0.066$) demonstrating the general equivalence of the participants used for the discovery and validation phases of the biomarker analysis.

TABLE 3

| Cognitive Measure | Normal Control (n = 73) | Converter$_{pre}$ (n = 28) | MCI/AD (n = 74) |
|---|---|---|---|
| Multiple Assessment Inventory IADL Scale (MAI-IADL) | 26.51 (1.71) | 26.65 (0.87) | 24.82 (3.60) |
| Multifactorial Memory Questionnaire (MMQ) | 130.32 (19.93) | 139.71 (13.36) | 121.01 (18.14) |
| Mini Mental State Examination (MMSE) | 28.64 (1.30) | 28.61 (2.49) | 26.32 (2.87) |
| Geriatric Depression Scale-Short Form (GDS-SF) | 1.47 (2.02) | 1.32 (2.28) | 1.97 (2.7) |
| Wechsler Memory Scale-III Forward Digit Span (WMS-III FDS) | 6.25 (1.05) | 6.18 (0.95) | 6.14 (1.13) |
| Trail Making Test- Part A (TMT-A) | 36.69 (13.23) | 46.14 (14.75) | 55.26 (44.63) |
| Wechsler Memory Scale-III Backward Digit Span (WMS-III BDS) | 4.34 (0.9) | 4.29 (0.76) | 4.01 (0.91) |
| Trail Making Test- Part B (TMT-B) | 98.53 (41.30) | 134.57 (63.89) | 151.99 (69.82) |
| Category fluency (Animals) | 20.91 (4.72) | 19.0 (5.24) | 15.16 (5.03) |
| Boston Naming Test 60-Item version (BNT-60) | 56.29 (3.19) | 53.14 (7.96) | 50.51 (9.46) |
| Rey Auditory Verbal Learning Test Learning (RAVLT Total Learning A1-A5) | 43.43 (7.76) | 37.0 (5.88) | 27..08 (7.01) |
| Rey Auditory Verbal Learning Test Delayed Recall (RAVLT Trial A7) | 7.84 (2.48) | 5.32 (2.59) | 1.93 (1.64) |
| Rey Auditory Verbal Learning Test Retention (RAVLT Recognition) | 13.30 (1.57) | 11.14 (2.24) | 7.09 (3.15) |
| Hooper Visual Organization Test (HVOT) | 23.96 (3.05) | 22.35 (3.72) | 20.93 (4.51) |

Lipidomic Definition of Participant Groups

The plasma samples from the 124 discovery phase participants were subjected to lipidomics analysis. In the discovery phase, metabolomic/lipidomic profiling yielded 2700 features in the positive mode and 1900 features in the negative mode. The metabolites that define the participant groups were selected from among ail known to be identifiable using a regularized learning technique, the least absolute shrinkage and selection operator (LASSO) penalty as implemented with the R package 'glmnet'. The LASSO analysis revealed features that assisted in unambiguous class separation between aMCI/AD, Converter$_{pre}$ and the NC group (Table 4).

TABLE 4

Putative metabolite markers resulting from binary comparison of the study groups

| Metabolite | Lasso Coefficient | Comparison Groups | Mode | Mass/Charge Ratio |
|---|---|---|---|---|
| PI (18:0/0:0) | ↓ (−0.674) | Normal vs Converter$_{pre}$ | NEG | 599.3226 |
| ProAsn | ↑ (0.192) | Normal vs aMCI/AD | POS | 230.1146 |

TABLE 4-continued

Putative metabolite markers resulting from binary comparison of the study groups

| Metabolite | Lasso Coefficient | Comparison Groups | Mode | Mass/Charge Ratio |
|---|---|---|---|---|
| Glycoursodeoxycholic acid | ↑ (0.107) | Normal vs aMCI/AD | POS | 450.3196 |
| Malic acid | ↓ (−0.024) | Normal vs aMCI/AD | POS | 134.0207 |

The markers in Table 1 were chosen based on the significant predictive value as determined by LASSO coefficient analysis. The positive estimated LASSO coefficient suggests elevation in corresponding comparison group (aMCI/AD and Converter$_{pre}$) compared to normal control (NC) participants. Up arrows indicate up-regulation in the comparison group as compared to the NC participants while the down arrow suggests down-regulation in these groups.

This untargeted lipidomic analysis revealed a significant decrease in the level of phosphatidyl inositol (PI) in the Converter$_{pre}$ group and an elevation in the plasma levels of glycoursodeoxycholic acid in the aMCI/AD patients as compared to the NC group. These metabolites were unambiguously identified using tandem mass spectrometry. The other metabolites that displayed differential abundance in the study groups consisted of amino acids, biogenic amines and a broad range of phospholipids and other lipid species that were putative identified based on accurate mass stringency of ≤5 ppm.

In the next step of the metabolomic/lipidomic analyses multiple reaction monitoring (MRM) was performed for stable isotope dilution-mass spectrometry (SID-MS) to unambiguously identify and quantify those metabolites such as lipids, amino acids and biogenic amines that function similar to those identified in the LASSO analysis and characterize the participant groups, with special emphasis on differences that would predict a predisposition of phenoconversion from NC to aMCI/AD, The data revealed significantly lower plasma levels of serotonin, taurine, phenylalanine, praline, lysine, phosphatidyl choline (PC) and acylcarnitine (AC) in Converter$_{pre}$ participants who later developed aMCI/AD. Conversely, these participants also showed an elevation in the levels of DOPA.

TABLE 5

Difference detection of putative metabolites using stable isotope dilution multiple reaction monitoring mass spectrometry (SID-MRM-MS).

| Metabolite | Fold Change | Comparison Groups | Mode | p-value |
|---|---|---|---|---|
| PC ae C38.4 | ↓ | Normal vs Converter$_{pre}$ | POS | 0.00417 |
| Proline | ↓ | Normal vs Converter$_{pre}$ | POS | 3.00E−05 |
| Lysine | ↓ | Normal vs Converter$_{pre}$ | POS | 0.0020 |
| Serotonin | ↓ | Normal vs Converter$_{pre}$ | POS | 0.0160 |
| Taurine | ↓ | Normal vs Converter$_{pre}$ | POS | 0.0030 |
| DOPA | ↑ | Normal vs Converter$_{pre}$ | POS | 0.00011 |
| Phenylalanine | ↓ | Normal vs Converter$_{pre}$ | POS | 1.00E−05 |
| Acylcarnitine C7-DC | ↓ | Normal vs aMCI/AD | POS | 0.0001 |

Up arrows in Table 5 indicate up-regulation in the comparison group as compared to the normal control (NC) participants while the down arrow suggests down-regulation in these groups.

The targeted metabolomic/lipidomic analysis identified of a set of ten metabolites, comprised of PCs, lyso PCs, and ACs that were depleted in the plasma of the Converter$_{pre}$ participants compared to the NC group. These metabolites remain depleted after the same participants phenoconverted to aMCI/AD (Converters$_{post}$) and were nearly equivalent to the low levels seen in the cognitively impaired aMCI/AD group. A simple logistic model with the ten metabolite panel was used to predict/classify Converter$_{pre}$ and NC participants. When displayed as a ROC curve, the ten metabolite panel comparing Converter$_{pre}$ and NC participants yielded an AUC of 0.96, while the panel yielded an AUC of 0.827 for the aMCI/AD vs NC classification.

Figure 3:
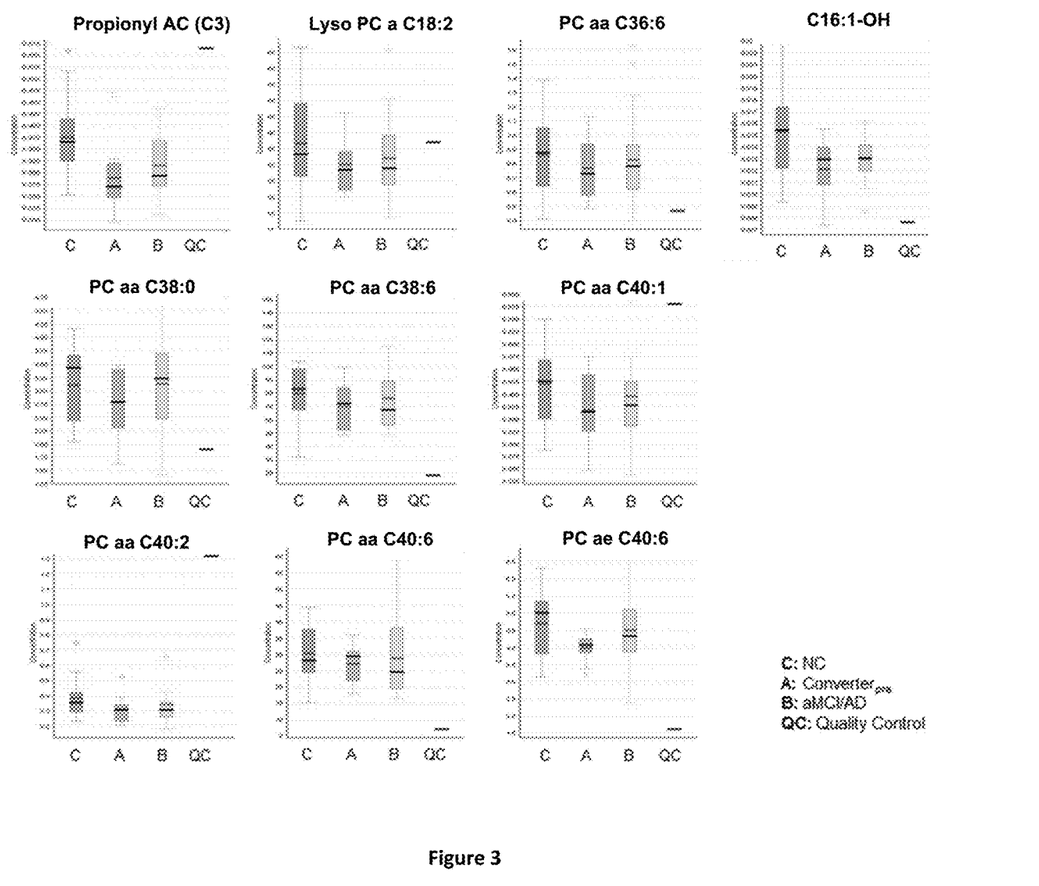
FIG. 3 depicts a trend plot for the ten metabolite panel-validation phase. This figure shows the results of the blinded, internal cross-validation for each of the ten metabolites using targeted quantitative mass spectrometry. The solid line represents the median abundance for the given group and the dotted line represents mean abundance. Three groups (A, B, C), which included NC (n=20), Converter$_{pre}$ (n=10), and aMCI/AD (n=20) were processed in a blinded manner. The differential abundance of metabolites was qualitatively compared to results from the discovery groups, allowing prediction of the unknown groups and matching to those in FIG. 2, which was confirmed after lifting the blind. QC shows the scatter in the quality control samples.

To confirm the reproducibility of the ten metabolite panel from the discovery samples, targeted quantitative metabolomics/lipidomics analyses was performed using plasma from the independent validation group of 40 participants as an independent cross validation. One sample from the MCI/AD group was not available for lipidomic analysis. The validation samples were obtained from the last available visit from the aMCI/AD, Converter$_{pre}$, and NC groups and were designated as groups A, B, and C and analyzed in a blinded fashion, without specification of diagnostic identities. The samples were processed and analyzed using the same SID-MRM-MS technique as in the discovery phase. The blinded data were analyzed to determine if the unknown groups could be characterized into the correct diagnostic categories based solely on the levels of the ten metabolite panel. The validation analysis revealed lower levels of the assayed metabolites in groups A and B compared to group C (FIG. 3). Based on these qualitative differences, it was predicted that group C was the NC group and groups A and B were Converter$_{pre}$ and aMCI/AD groups, respectively. Subsequent un-blinding of the groups confirmed these predictions.

Figure 4:
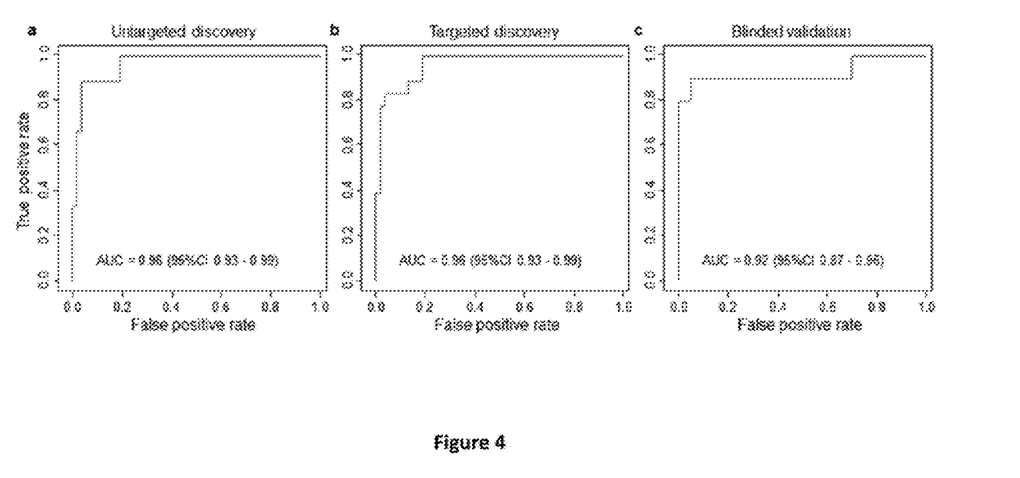

The metabolomic data was used from the untargeted LASSO analysis to build separate linear classifier models that would distinguish the aMCI/AD group from the NC group and the Converter$_{pre}$ group from the NC group. A receiver operating characteristic (ROC) analysis was employed to determine the area under the ROC curve (AUC) to assess the performance of the classifier models in differentiating the groups. When distinguishing between the Converter$_{pre}$ and NC groups, the LASSO identified metabolites yielded an AUC of 0.96 (FIG. 4a), and 0.83 when distinguishing the a MCI/AD and NC groups. These high AUC values demonstrate robust discrimination between the aMCI/AD, Converter$_{pre}$, and NC groups by the models. Using the same linear classifier method, a simple logistic model was constructed using just the ten metabolite panel and used this to classify the same groups. When displayed as a ROC curve, the ten metabolite panel classified Converter$_{pre}$ and NC participants with an AUC of 0.96 (FIG. 4b), while the panel yielded an AUC of 0.827 for the aMCI/AD vs NC classification.

The effects of apolipoprotein epsilon (ApoE) genotype was considered. ApoE is involved in lipid metabolism and is a known risk factor for Alzheimer's Disease and ApoE genotype status was accounted for by repeating this classification analysis with APO −ε4 presence as a covariate and it was found the classification accuracy changed only minimally from 0.96 to 0.968 (p=0.992). Furthermore, a classifier model using only APO −ε4 produced an AUC of 0.54 for classifying the Converter$_{pre}$ and NC groups implying virtually random classification. These findings clearly indicate that the presumed pathophysiology reflected by the ten metabolite biomarker panel is independent of ApoE mediated effects. Finally, the same simple logistic classifier model developed for the discovery samples was applied to the independent validation samples. The ROC constructed from the validation group data classified Converter$_{pre}$ and NC participants with an AUC of 0.92 and 0.77 for classifying the aMCI/AD vs NC groups. For a specificity of 90%, the ten metabolite panel yielded a sensitivity of 83.3% for correct classification of the Converter$_{pre}$ and NC participants in the discovery phase and a sensitivity of 90% in the validation phase.

What is claimed is:

1. A method of treating memory impairment associated with a neurodegenerative disorder in a subject prior to the onset of memory impairment in the subject comprising
   (a) analyzing at least one sample from the subject prior to the onset of any signs of memory impairment to determine the levels of a collection of lipid metabolites in a subject, wherein the collection of lipid metabolites comprises the metabolites C16:1-OH, PC aa C38:0, PC aa C38:6 and PC ae C40:6, and
   (b) administering a treatment for memory impairment when the levels of each of the lipid metabolites are lower than normal levels of each of the lipid metabolites, wherein the normal levels of lipid metabolites are established from either (i) the subject's levels of lipid metabolites that are determined prior to the onset of any signs of memory impairment and prior to analyzing the at least one sample in (a), or (ii) levels of lipid metabolites that are measured in a population of individuals that do not display memory impairment.

2. The method of claim 1, wherein the collection of lipid metabolites in the subject is analyzed at more than one time point prior to the onset of any signs of memory impairment, wherein a plasma sample is obtained from the subject at each time point.

3. The method of claim 1 or 2, wherein the collection of lipid metabolites is analyzed in the samples by mass spectroscopy or high-performance liquid chromatography (HPLC).

4. The method of claim 3, wherein the collection of lipid metabolites further comprises at least one additional metabolite selected from the group consisting of propionyl AC, lyso PC a C18:2, PC aa C36:6, PC aa C40:1, PC aa C40:2 and PC aa C40:6.

5. The method of claim 4, wherein the collection of lipid metabolites comprises propionyl AC, lyso PC a C18:2, PC aa C36:6, C16:1-OH, PC aa C38:0, PC aa C38:6, PC aa C40:1, PC aa C40:2, PC aa C40:6 and PC ae C40:6.

6. The method of claim 1, further comprising continuing administration of the treatment to the subject after the onset of any detectable signs of memory impairment in the subject.

7. The method of claim 1, wherein the sample is a plasma sample.

8. The method of claim 1, wherein the collection of lipid metabolites consists of propionyl AC, lyso PC a C18:2, PC aa C36:6, C16:1-OH, PC aa C38:0, PC aa C38:6, PC aa C40:1, PC aa C40:2, PC aa C40:6 and PC ae C40:6.

9. The method of claim 1, wherein the neurodegenerative disorder is Alzheimer's disease.

10. A method of treating memory impairment associated with mild cognitive impairment in a subject prior to the onset of memory impairment in the subject comprising
    (a) analyzing at least one sample from the subject prior to the onset of any signs of memory impairment to determine the levels of a collection of lipid metabolites in a subject, wherein the collection of lipid metabolites comprises the metabolites C16:1-OH, PC aa C38:0, PC aa C38:6 and PC ae C40:6, and (b) administering a treatment for memory impairment when the levels of each of the lipid metabolites are lower than normal levels of each of the lipid metabolites, wherein the normal levels of lipid metabolites are established from either (i) the subject's levels of lipid metabolites that are determined prior to the onset of any signs of memory impairment and prior to analyzing the at least one sample in (a), or (ii) levels of lipid metabolites that are measured in a population of individuals that do not display memory impairment.

11. The method of claim 10, wherein the collection of lipid metabolites in the subject is analyzed at more than one time point prior to the onset of any signs of memory impairment, wherein a plasma sample is obtained from the subject at each time point.

12. The method of claim 10 or 11, wherein the collection of lipid metabolites is analyzed in the samples by mass spectroscopy or high-performance liquid chromatography (HPLC).

13. The method of claim 12, wherein the collection of lipid metabolites further comprises at least one additional metabolite selected from the group consisting of propionyl AC, lyso PC a C18:2, PC aa C36:6, PC aa C40:1, PC aa C40:2 and PC aa C40:6.

14. The method of claim 13, wherein the collection of lipid metabolites comprises propionyl AC, lyso PC a C18:2, PC aa C36:6, C16:1-OH, PC aa C38:0, PC aa C38:6, PC aa C40:1, PC aa C40:2, PC aa C40:6 and PC ae C40:6.

15. The method of claim 10, wherein the collection of lipid metabolites consists of propionyl AC, lyso PC a C18:2, PC aa C36:6, C16:1-OH, PC aa C38:0, PC aa C38:6, PC aa C40:1, PC aa C40:2, PC aa C40:6 and PC ae C40:6.

16. The method of claim 10, further comprising continuing administration of the treatment to the subject after the onset of any detectable signs of memory impairment in the subject.

17. The method of claim 10, wherein the sample is a plasma sample.

18. The method of claim 10, wherein the mild cognitive impairment is amnesiac mild cognitive impairment.

* * * * *

UNITED STATES PATENT AND TRADEMARK OFFICE
CERTIFICATE OF CORRECTION

PATENT NO. : 10,578,629 B2
APPLICATION NO. : 15/134976
DATED : March 3, 2020
INVENTOR(S) : Howard J. Federoff et al.

It is certified that error appears in the above-identified patent and that said Letters Patent is hereby corrected as shown below:

In the Specification

At Column 1, Lines 6-10, delete the following paragraph:
"Part of the work performed during development of this invention utilized U.S. Government funds under National Instituted of Health Grant No. R01 AG030753 and Department of Defense Contract No. W81XWH-09-1-0107. The U.S. Government has certain rights in this invention."
And insert in its place the following paragraph:
--This invention was made with government support under grant number AG030753 awarded by the National Institutes of Health and grant number W81XWH-09-1-0107 awarded by the Department of Defense. The government has certain rights in the invention.--

Signed and Sealed this
Sixth Day of February, 2024

Katherine Kelly Vidal
*Director of the United States Patent and Trademark Office*